United States Patent [19]

Tadanier et al.

[11] 4,263,429

[45] Apr. 21, 1981

[54] 1,2,6-TRI-N-BENZYLOXYCARBONYLFOR-TIMICIN B-4,5-CARBAMATE AND 1,2,6-TRI-N-ACETYLFORTIMICIN B-4,5-CARBAMATE

[75] Inventors: John S. Tadanier; Jerry R. Martin, both of Waukegan, Ill.

[73] Assignee: Abbott Laboratories, North Chicago, Ill.

[21] Appl. No.: 79,137

[22] Filed: Sep. 26, 1979

[51] Int. Cl.³ .......................................... C07H 15/22
[52] U.S. Cl. ................................. 536/17 R; 548/221; 424/180
[58] Field of Search ................ 548/221; 424/180, 118; 536/17 R, 17 B

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,091,032 | 5/1978 | Tadanier et al. | 424/118 |
| 4,169,198 | 5/1979 | Martin et al. | 536/17 R |
| 4,176,178 | 11/1979 | Martin et al. | 424/180 |
| 4,187,296 | 2/1980 | Tadanier et al. | 424/180 |
| 4,187,297 | 2/1980 | Martin et al. | 424/180 |
| 4,187,298 | 2/1980 | Martin et al. | 424/180 |
| 4,187,299 | 2/1980 | Post | 424/181 |
| 4,192,867 | 3/1980 | Martin et al. | 424/180 |

*Primary Examiner*—Mary C. Lee
*Attorney, Agent, or Firm*—Robert L. Niblack; Gildo E. Fato; Joyce R. Niblack

[57] ABSTRACT

A fortimicin intermediate selected from the group consisting of 1,2',6'-tri-N-benzyloxycarbonylfortimicin B-4,5-carbamate and 1,2',6'-tri-N-acetylfortimicin A-4,5-carbamate. The compounds are useful as intermediates in the preparation of 2-epi-fortimicin B.

3 Claims, No Drawings

1,2,6-TRI-N-BENZYLOXYCARBONYLFORTIMICIN B-4,5-CARBAMATE AND 1,2,6-TRI-N-ACETYLFORTIMICIN B-4,5-CARBAMATE

BACKGROUND OF THE INVENTION

Aminoglycoside antibiotics have proven to be a valuable class of antibiotics which include the streptomycins, kanamycins, neomycins, gentamicins, tobramycins, amikacin and the more recently discovered fortimicins. As with other classes of antibiotics, chemical modification of the parent antibiotics has been found to advantageously alter either the pharmacological properties or the antibacterial properties of many of the naturally produced aminoglycoside antibiotics either by increasing their antibacterial spectrum, increasing their intrinsic activity, increasing their activity against resistant strains or providing compounds which are less toxic than the parent antibiotics.

Chemical modification has been found to be of value in the fortimicin family of antibiotics as well. See for example, U.S. Pat. Nos. 4,091,032 and 4,124,746, 4,192,867; 4,169,198; 4,183,920; 4,176,178; 4,187,296; 4,187,298; 4,187,297 and 4,187,299 and allowed, commonly assigned, co-pending application Ser. Nos. 863,015, Ser. No. 863,014

Another valuable modification is disclosed in commonly assigned, co-pending application Ser. No. 25,236 filed March 29, 1979, now abandoned, which claims 2-epi-fortimicin A, 2-epi-fortimicin B and 2-epi-4-N-acyl and alkylfortimicin B derivatives. The present invention provides two intermediates useful in the preparation of the 2-epi-fortimicins A and B.

SUMMARY OF THE INVENTION

The present invention provides two fortimicin intermediates, 1,2',6'-tri-N-benzyloxycarbonylfortimicin B-4,5-carbamate and 1,2',6'-tri-N-acetylfortimicin B-4,5-carbamate. The compounds are useful as intermediates in the preparation of 2-epi-fortimicin B.

DETAILED DESCRIPTION OF PREFERRED EMBODIMENTS

The compounds of this invention, 1,2',6'-tri-N-benzyloxycarbonylfortimicin B and 1,2',6'-tri-N-acetylfortimicin B-4,5-carbamate are represented by formula

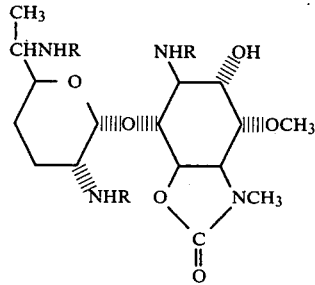

wherein each R is benzyloxycarbonyl or each R is acetyl with the limitation that all R's must be benzyloxycarbonyl or all R's must be acetyl.

The preparation of the intermediates of this invention is detailed in the following examples and summarized in the following reaction schemes.

Generally speaking, 2-epi-fortimicin B can be prepared from one of the intermediates of this invention as follows. 1,2',6'-tri-N-benzyloxycarbonylfortimicin B-4,5-carbamate is converted to the corresponding 2-O-methansulfonate. Solvolysis of the latter in aqueous 1,2-dimethoxyethane in the presence of ammonium acetate gives approximately equimolar mixture of 1,2',6'-tri-N-benzyloxycarbonyl-2-epi-4,5-carbamate and 2,6'-di-N-benzyloxycarbonyl-2-epi-biscarbamate. Alternatively, when the solvolysis of the 2-O-methanesulfonate derivative is carried out in a mixture with aqueous tetrahydrofuran and sodium bicarbonate, the 2-epi-oxzoline is formed. When the latter is heated under reflux in a solution prepared from ammonium acetate and aqueous 1,2-dimethoxyethane, an approximately equimolar mixture of 2-epi-4,5-carbamate and the 2-epi-bis-carbamate is formed.

The mixture of 2-epi-mono and biscarbamates may then be separated into the pure components by chromatography. Alternatively, the mixture can be heated under reflux with a mixture of sodium bicarbonate and methanol and the monocarbamate converted the the bis-carbamate which may then be isolated by chromatography.

Hydrogenolysis of the resulting 1,2'-di-N-benzyloxycarbonyl-2-epi-fortimicin B-bis-carbamate with 5% Pd/C in the presence of 0.2 N-methanolic hydrochloric acid gives 2-epi-fortimicin B dihydrochloride which in turn is an intermediate in the preparation of 2-epi-fortimicin A and 2-epi-fortimicin B derivatives as disclosed in co-pending commonly assigned patent application Ser. No. 25,236 filed March 29, 1979, now abandoned.

Briefly, 2-epi-fortimicin B is converted to 1,2',6'-tri-N-benzyloxycarbonylfortimicin B with N-benzyloxycarbonyloxysuccinimide, following the general procedure described in U.S. Pat. No. 4,091,032. Catalytic hydrogenation of the resulting products, tetra-N-benzyloxycarbonyl-2-O-[N-benzyloxycarbonylglycyl]-2-epi-fortimicin A and tetra-N-benzyloxycarbonyl-2-epi-fortimicin A, with 5% Pd/C in 0.2 N methanolic hydrochloric acid yields 2-O-glycyl-2-epi-fortimicin A and 2-epi-fortimicin A, respectively, isolated as their perhydrochloride salts.

Alternatively, fortimicin B is converted to tetra-N-acetylfortimicin B by known methods. Selective hydrolysis of the latter with sodium bicarbonate in aqueous methanol gives 1,2',6'-tri-N-acetylfortimicin B which is converted to the corresponding 4-N-ethoxycarbonyl derivative which is then readily cyclized to the 4,5-carbamate in a refluxing suspension of sodium bicarbonate in aqueous methanol. Treatment of the carbamate with methanesulfonic anhydride in pyridine results in the 2-epi-1,2-oxazoline derivative of the carbamate and hydrolysis of the latter with aqueous hydrochloric acid in tetrahydrofuran results in 1,2',6'-tri-N-acetyl-2-epi-fortimicin B-4,5-carbamate. The latter is converted to the 2-O-benzyl ether with benzylbromide and barium hydroxide. Hydrolysis of the latter with aqueous sodium hydroxide resulted in 2-O-benzyl-2-epi-fortimicin B. Treatment of the latter with N-benzyloxycarbonyloxysuccinimide results in 1,2',6'-tri-N-benzyloxycarbonyloxy-2-epi-fortimicin B. Treatment of the latter with the N-hydroxysuccinimide ester of N-benzyloxycarbonylglycine results in tetra-N-benzyloxycarbonyl-2-O-benzyl-2-epi-fortimicin A which is converted to 2-epi-fortimicin A tetrahydrochloride as described above.

The preparation of the intermediates of this invention are summarized in the following reaction schemes:

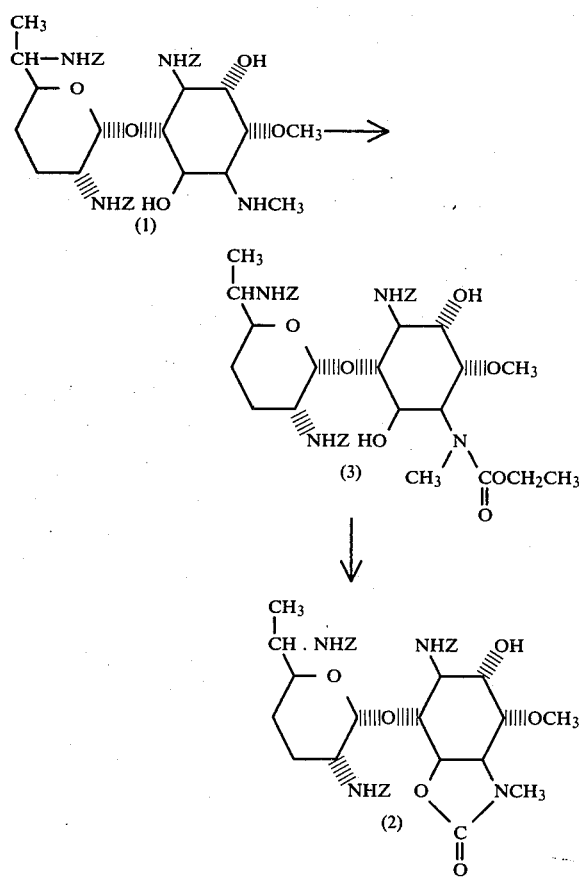

The following examples further illustrate the present invention.

EXAMPLE 1

1,2',6'-Tri-N-benzyloxycarbonylfortimicin B (1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° C. for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide [23.4:1.4:0.1(v/v/v)] gives 1.05 g of product (1): $[\alpha]_D^{25}$ −16.5° (c 1.0, $CH_3OH$); IR($CDCl_3$) 1712 and 1507 $cm^{-1}$; NMR($CDCl_3$) δ 1.03 ($C_{6'}$—$CH_3$, $J_{6'7'}=6.0$ Hz), 2.32 ($C_4$—$NCH_3$), 3.41 ($OCH_3$).

Analysis Calcd. for $C_{39}H_{50}N_4O_{11}$: C, 62.39; H, 6.71; N, 7.46; Found: C, 62.16; H, 6.76; N, 7.43

EXAMPLE 2

1,2',6'-Tri-N-benzyloxycarbonylfortimicin B-4,5-carbamate (2)

A magentically stirred solution of 18.2 g of 1,2',6'-tri-N-benzyloxycarbonylfortimicin B (1), 12.6 g of sodium bicarbonate, 8.1 ml of ethyl chloroformate, and 750 ml of methanol is kept overnight at room temperature and then heated under reflux for 1.5 hours. The solvent is evaporated under reduced pressure and the residue is washed with 600 ml of chloroform. The resulting suspension is filtered and the chloroform is evaporated from the filtrate leaving 16.7 g of the desired product (2). An analytical sample is prepared by chromatographing 1.08 g of material on a column of 100 g of silica gel packed and eluted with a system of benzene-ethanol[9:1(v/v)] to give 602 mg of product of analytical quality and 405 mg of material suitable for further reaction: $[\alpha]_D^{22}+2.5°$ (c 1%, $CH_3OH$); NMR($CDCl_3$)δ0.98d(J=6.0)($C_{6'}$—$CH_3$), 2.83($NCH_3$), 3.44($OCH_3$); IR($CDCl_3$) 3562,3438,3320,1759,1706 $cm^{-1}$.

Analysis Calcd. for $C_{40}H_{48}N_4O_{12}$: C, 61.84; H, 6.23; N, 7.21. Found: C, 61.62; H, 6.36; N, 7.16.

B. A solution of 13.0 g of 4-N-ethoxycarbonyl-1,2',6'-tri-N-benzyloxycarbonylfortimicin B (3), 5.3 g of sodium bicarbonate and 370 ml of methanol is heated under reflux for 1.5 hours. The methanol is evaporated under reduced pressure and the residue triturated with chloroform. The chloroform suspension are filtered. Evaporation of the chloroform from the filtrate gives 12.1 g of product. The latter is chromatographed on 850 g of silica gel using a solvent system prepared from benzene-ethanol[9:1(v/v)] to yield 10.9 g of pure product, identical with that characterized above.

EXAMPLE 3

1,2',6'-Tri-N-acetylfortimicin B-4,5-carbamate

A magnetically stirred mixture of 33.4 g of tetra-N-acetylfortimicin B, prepared by the method of R. S. Egan et al., *J. Antibiotics,* No. 7,552(1977), 20 g of sodium bicarbonate, 300 ml of water and 1 liter of methanol is heated under reflux overnight. The major portion of the solvent is evaporated under reduced pressure, and residual water is removed by codistillation with several portions of ethanol under reduced pressure. The residue is triturated with several portions of warm chloroform. The supernatant is filtered and evaporated to dryness under reduced pressure leaving 29.1 g of crude 1,2',6'-tri-N-acetylfortimicin B.

A sample (5.13 g) of the crude product is chromatographed on a column of 400 g of silica gel, packed and eluted with a solvent system composed of chloroform-95% aqueous methanol-ammonium hydroxide (concentrated)[18:6:0.5(v/v/v)] to yield 4.37 g of pure product: $[\alpha]_D^{21.2}+27.8$(c 1%, $CH_3OH$); IR($CDCl_3$) 3553,3439,3333,1655 $cm^{-1}$; NMR($CDCl_3$) δ1.16d(J=3 Hz, $C_{6'}$—$CH_3$); 1.94, 1.98, 1.99 ($OCOCH_3$'s); 2.41($NCH_3$); 3.45($OCH_3$); 5.2 d(J=3 Hz, $C_{1'}$—H).

We claim:

1. A fortimicin intermediate selected from the group consisting of 1,2',6'-tri-N-benzyloxycarbonylfortimicin B-4,5-carbamate and 1,2',6'-tri-N-acetylfortimicin B-4,5-carbamate.

2. 1,2',6'-Tri-N-benzyloxycarbonylfortimicin B-4,5-carbamate.

3. 1,2',6'-Tri-N-acetylfortimicin B-4,5-carbamate.

* * * * *